(12) United States Patent
Charles

(10) Patent No.: US 8,298,253 B2
(45) Date of Patent: Oct. 30, 2012

(54) VARIABLE DRIVE VITRECTOMY CUTTER

(75) Inventor: Steven T. Charles, Memphis, TN (US)

(73) Assignee: Alcon Research, Ltd., Fort Worth, TX (US)

( * ) Notice: Subject to any disclaimer, the term of this patent is extended or adjusted under 35 U.S.C. 154(b) by 101 days.

(21) Appl. No.: 12/788,645

(22) Filed: May 27, 2010

(65) Prior Publication Data

US 2011/0295296 A1 Dec. 1, 2011

(51) Int. Cl.
*A61B 17/32* (2006.01)
*A61B 17/20* (2006.01)

(52) U.S. Cl. .......................................... 606/171; 604/22

(58) Field of Classification Search .................. 606/159, 606/160, 170, 171, 175, 176, 178, 179, 180; 604/22, 30, 32
See application file for complete search history.

(56) References Cited

U.S. PATENT DOCUMENTS

| | | | |
|---|---|---|---|
| 3,884,238 A | 5/1975 | O'Malley et al. | |
| 4,493,698 A | 1/1985 | Wang et al. | |
| 4,577,629 A | 3/1986 | Martinez | |
| 4,696,298 A | 9/1987 | Higgins et al. | |
| 4,757,814 A | 7/1988 | Wang et al. | |
| 4,819,635 A | 4/1989 | Shapiro | |
| 4,841,984 A | 6/1989 | Armeniades et al. | |
| 4,909,249 A | 3/1990 | Akkas et al. | |
| 4,940,468 A | 7/1990 | Petillo | |
| 4,986,827 A | 1/1991 | Akkas et al. | |
| 5,019,035 A | 5/1991 | Missirlian et al. | |
| 5,020,535 A | 6/1991 | Parker et al. | |
| 5,047,008 A | 9/1991 | de Juan, Jr. et al. | |
| 5,059,204 A | 10/1991 | Lawson et al. | |
| 5,061,238 A | 10/1991 | Shuler | |
| 5,176,628 A | 1/1993 | Charles et al. | |
| 5,284,472 A | 2/1994 | Sussman et al. | |
| 5,354,268 A | 10/1994 | Peterson et al. | |
| 5,380,280 A | 1/1995 | Peterson | |
| 5,423,844 A | 6/1995 | Miller | |
| 5,474,532 A | 12/1995 | Steppe | |
| 5,520,652 A | 5/1996 | Peterson | |
| 5,630,827 A | 5/1997 | Vijfvinkel | |
| 5,674,194 A | 10/1997 | Jung et al. | |
| 5,733,297 A | 3/1998 | Wang | |
| 5,782,849 A | 7/1998 | Miller | |
| 5,833,643 A * | 11/1998 | Ross et al. ....................... | 604/22 |
| 6,010,496 A | 1/2000 | Appelbaum et al. | |
| 6,514,268 B2 | 2/2003 | Finlay et al. | |
| 6,629,986 B1 | 10/2003 | Ross et al. | |
| 6,773,445 B2 | 8/2004 | Finlay et al. | |
| 7,743,847 B2 * | 6/2010 | Fisher .......................... | 173/205 |
| 2009/0287233 A1 | 11/2009 | Huculak | |

* cited by examiner

*Primary Examiner* — Tuan V Nguyen
(74) *Attorney, Agent, or Firm* — W. David Lee

(57) ABSTRACT

A vitrectomy probe having a variable duty cycle cutting mechanism is disclosed. The probe includes a motor and a cam driver rotationally driven by the motor. The cam driver has a non-planar driver surface having surface features that vary at different radii. A follower mechanism is arranged to selectively interface with the driver surface at different radii on the driver surface in a manner to selectively interface with the varied surface features at the different radii. The follower is arranged to transfer rotational movement of the cam driver into linear movement of the follower mechanism.

18 Claims, 4 Drawing Sheets

VARIABLE DRIVE VITRECTOMY CUTTER

BACKGROUND OF THE INVENTION

The present invention pertains to vitrectomy probes. More particularly, but not by way of limitation, the present invention pertains to a variable drive vitrectomy probe.

Microsurgical procedures frequently require precision cutting and/or removing various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g. cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. Such probes, frequently referred to as vitrectomy probes, are typically inserted via an incision in the sclera near the pars plana. The surgeon may also insert other microsurgical instruments such as a fiber optic illuminator, an infusion cannula, or an aspiration probe during the posterior segment surgery. While performing the surgery, the surgeon views the eye under a microscope.

Conventional vitrectomy probes typically include a hollow outer cutting member, a hollow inner cutting member arranged coaxially with and movably disposed within the hollow outer cutting member, and a port extending radially through the outer cutting member near the distal end thereof. Vitreous humor and/or membranes are aspirated into the open port, and the inner member is actuated, closing the port. Upon the closing of the port, cutting surfaces on both the inner and outer cutting members cooperate to cut the vitreous and/or membranes, and the cut tissue is then aspirated away through the inner cutting member. U.S. Pat. Nos. 4,577,629 (Martinez); 5,019,035 (Missirlian et al.); 4,909,249 (Akkas et al.); 5,176,628 (Charles et al.); 5,047,008 (de Juan et al.); 4,696,298 (Higgins et al.); and 5,733,297 (Wang) all disclose various types of vitrectomy probes, and each of these patents is incorporated herein in its entirety by reference.

These conventional vitrectomy probes can be divided into two types: "guillotine style" probes and rotational probes. A guillotine style probe has an inner cutting member that reciprocates along its longitudinal axis. A rotational probe has an inner cutting member that reciprocates around its longitudinal axis. In both types of probes, the inner cutting members are actuated using various methods. For example, the inner cutting member can be electromechanically actuated between the open and closed port positions using a conventional rotating electric motor or a solenoid. U.S. Pat. No. 6,629,986 discloses one example of a motor driven probe for performing ophthalmic procedures.

Despite the above described advances, a need still exists for improved vitrectomy probes. In particular, vitrectomy probes that allow a surgeon to continuously vary operational parameters are particularly desired.

The present disclosure is directed to addressing one or more of the deficiencies in the prior art.

SUMMARY OF THE INVENTION

In one exemplary aspect consistent with the principles herein, the present disclosure is directed to a vitrectomy probe having a variable duty cycle cutting mechanism. The probe includes a motor and a cam driver rotationally driven by the motor. The cam driver has a non-planar driver surface having surface features that vary at different radii. A follower mechanism is arranged to selectively interface with the driver surface at different radii on the driver surface in a manner to selectively interface with the varied surface features at the different radii. The follower is arranged to transfer rotational movement of the cam driver into linear movement of the follower mechanism. The probe also includes a cutting mechanism. The cutting mechanism includes an outer tubular member having a port configured to receive ophthalmic tissue and an inner tubular cutting member disposed within the outer tubular member. The inner tubular member is associated with the follower mechanism in a manner that the follower mechanism drives the inner tubular cutting member in an oscillating motion.

In another exemplary aspect consistent with the principles herein, the present disclosure is directed to an electric vitrectomy probe including an electrically powered motor and a cam driver rotationally driven by the motor. The cam driver includes a non-planar driver surface. The non-planar driver surface has a first radius with surface features resulting in a first duty cycle and a second radius with surface features resulting in a second duty cycle. A follower mechanism is arranged to interface selectively with both the first radius and the second radius. It is arranged to transfer rotational movement of the cam driver into linear movement of the follower mechanism. An actuating system is associated with one of the follower and the cam driver. The actuating system is structurally configured to move the follower and cam driver relative to each other from a position where the follower interfaces with the first radius of the cam driver to a position where the follower interfaces with the second radius. A cutting mechanism is associated with the follower and configured to cut tissue during a vitrectomy procedure.

In another exemplary aspect consistent with the principles herein, the present disclosure is directed to a method of operating a vitrectomy probe having a variable duty cycle cutting mechanism. The method includes inserting a cutting tube of the vitrectomy probe into a posterior segment of the eye and controlling a motor to rotationally drive a cam driver associated with the motor. The cam driver includes a non-planar driver surface having continuously variable surface features between a first radius with surface features resulting in a first duty cycle and a second radius with surface features resulting in a second duty cycle. The method includes actuating a system associated with one of a follower and the cam driver. The actuating system is structurally configured to move the follower and cam driver relative to each other from a position where the follower interfaces with the first radius of the cam driver to a position where the follower interfaces with the second radius to change the duty cycle from the first duty cycle to the second duty cycle or any radius and therefore duty cycle between these two limits. The method also includes opening and closing a port on a cutting tube in accordance with the first duty cycle when the follower is in contact with the first radius and opening and closing the port in accordance with the second duty cycle when the follower is in contact with the second radius.

It is to be understood that both the foregoing general description and the following detailed description are exemplary and explanatory only and are intended to provide further explanation of the invention as claimed. The following description, as well as the practice of the invention, sets forth and suggests additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to exemplary embodiments of the invention, examples of which are illustrated in the accompanying drawings. Wherever possible, the same reference numbers are used throughout the drawings to refer to the same or like parts.

The present disclosure is directed to a surgical probe having a continuously variable duty cycle. Ophthalmic surgeries frequently require treating tissue both spaced from and adjacent to the retina. The tissue spaced from the retina may be treated with the probe operating at a first or relatively higher duty cycle because the sensitivities of the eye are less pronounced. Accordingly, efficiencies are achieved by operating at a higher duty cycle. However, because the fibrils of ophthalmic tissue are connected to other ophthalmic tissue and eventually to the retina, it has been discovered that treating tissue at areas adjacent to the retina can be more appropriately accomplished using a second or relatively lower duty cycle. Lower duty cycles result in less disruption to the retina. As used herein, "duty cycle" refers to the amount of time that an outer port is open to receive tissue during each cut cycle divided by the total amount of time in each cut cycle.

The system and method herein permit a health care provider to continuously vary or modify the duty cycle from a first duty cycle to a second duty cycle in an electric vitrectomy cutter. This may be done on-the-fly, and does not require disassembly to switch components, as does the prior art. This results in more efficient surgeries, potentially resulting in lower expenses to the patient.

Figure 1:
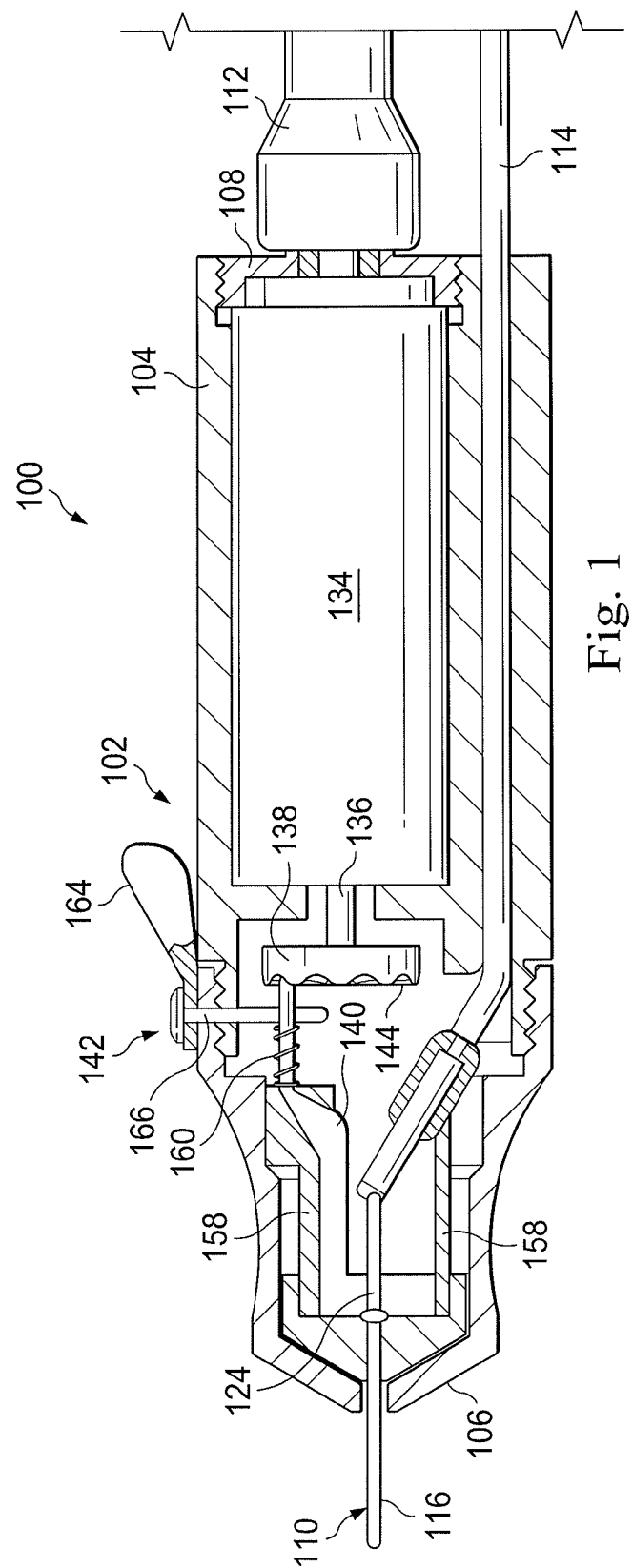
FIG. 1 is an illustration of an exemplary surgical probe of the present invention in cross-section implementing the principles and methods described herein.

FIG. 1 shows a cross-sectional view of an exemplary vitrectomy probe 100 according to the principles disclosed herein. The probe 100 is used to remove and aspirate tissue, and finds particular utility for removing intraocular tissue during an ophthalmic procedure to re-attach a retina of an eye. Although use in an ophthalmic procedure is described, it is to be understood that the probe 100 can be used to cut and aspirate other tissue, such as removing polyps, fibroids and other human tissue.

The probe 100 includes a main housing 102 including a hand piece 104 and distal and proximal caps 106, 108. A cutting tube 110 extends from the distal cap 106, and in the example shown, a power cord 112 and aspiration line 114 extend from the proximal cap 108. The power cord 112 may connect to an ophthalmology surgical console (not shown). In some embodiments, instead of using a power cord, electric power is drawn from an attached battery or other source.

Figure 2:
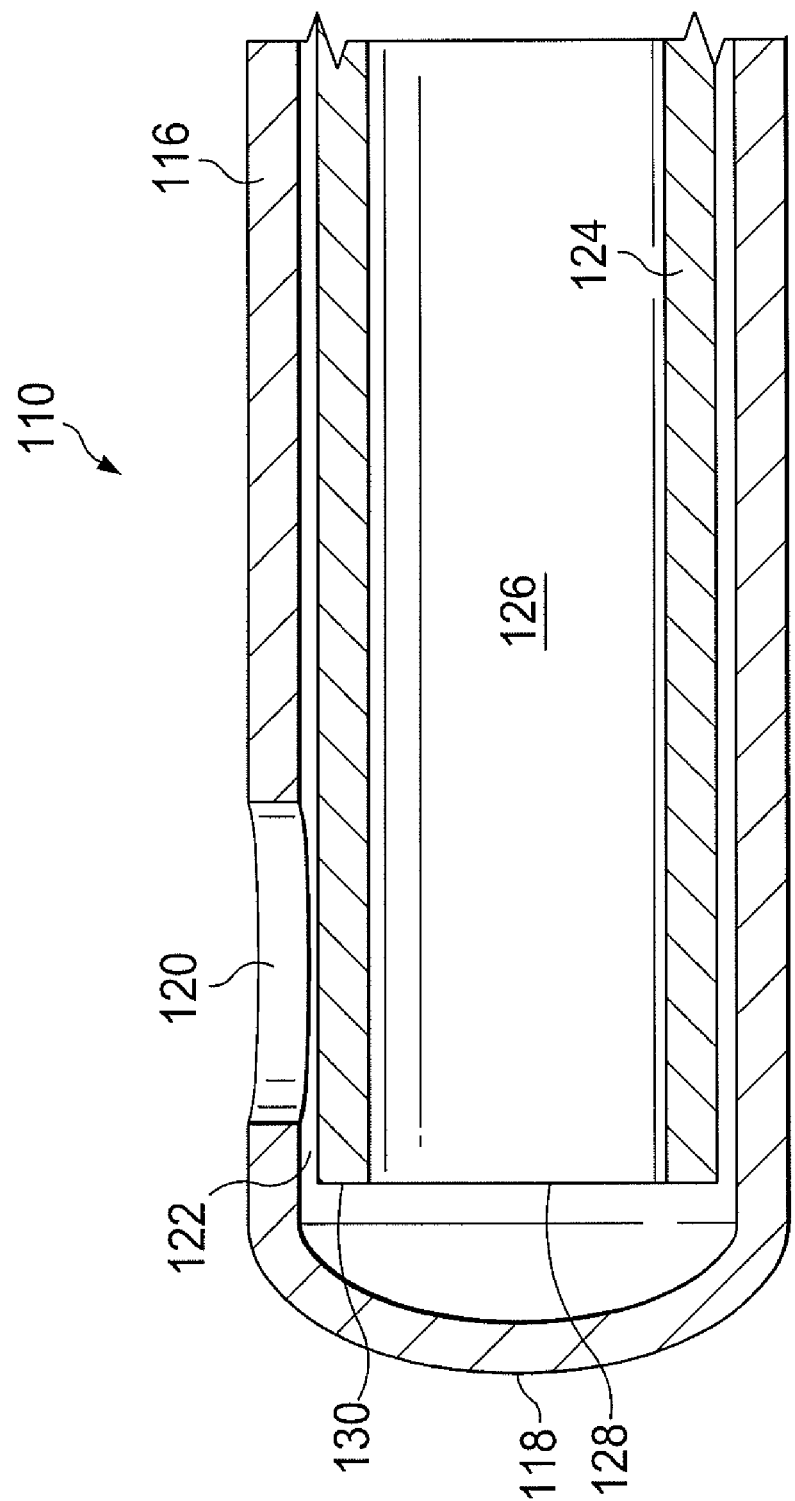
FIG. 2 is an illustration of a sectional view of a distal end of a cutter of the probe of FIG. 1.

A distal end of the cutting tube 110 is shown in FIG. 2. The cutting tube 110 includes an outer sleeve 116 that has a closed end 118, and an outer port 120 that receives tissue, such as ophthalmic tissue. The outer port 120 is in fluid communication with an inner channel 122 of the outer sleeve 116. An inner cutting member 124 is located within the inner channel 122 of the outer sleeve 116. The inner cutting member 124 has an inner bore 126, an open end 128, and a cutting surface 130. The inner bore 126 is in fluid communication with the aspiration line 114 (FIG. 1). The aspiration line 114 connects to a vacuum pressure that pulls tissue into the outer port 120 when the inner cutting member 124 is located away from the port 120. The inner cutting member 124 moves within the inner channel 122 of the outer sleeve 116 to cut tissue that is pulled into the outer port 120 by the aspiration system. The ophthalmic tissue received by the outer port 120 is preferably vitreous or membranes.

When used to cut tissue, the inner cutting member 124 is initially moved away from the outer port 120 and the vacuum pressure pulls tissue into the port 120 and the inner channel 122. The inner cutting member 124 then moves toward the outer port 120 and severs the tissue within the inner channel 122. The severed tissue is pulled through the inner bore 126 of the inner cutting member 124 by the aspiration system. The inner cutting member 124 then moves away from the outer port 120, and the cutting process is repeated. A cutting cycle includes moving the inner cutting member 124 to open the port 120 and then moving the cutting member 124 to close the port 120 to initiate the cut and return the cutting member 124 to its starting position for the next cutting cycle.

The actuation of the inner cutting member 124 opens the port 120 for a fixed amount of time in each cut cycle of the probe 100. In some embodiments, for a given vacuum level or a given flow rate, this results in a relatively consistent volume of cut ophthalmic tissue regardless of the probe cut rates. The amount of time the port 120 is open in each cut cycle is preferably about 1.5 milliseconds to about 2.5 milliseconds.

Returning to FIG. 1, the probe's main housing 102 includes variable duty cycle system comprising a motor 134 having a rotating output shaft 136, a cam driver 138, a follower or slider 140, and an actuating system 142.

In the probe 100, the motor 134 drives the oscillating movement of the inner cutting member 124. To do this, as expected, the motor 134 rotates the output shaft 136. The cam driver 138 and the follower 140 convert the rotational movement from the output shaft 136 to a linear movement that drives the inner cutting member 124 of the probe 100. In this embodiment, the motor 134 is an electric drive motor that is coupled to an external power source by the power cord 112. The rotational speed of the output shaft 136 is a function of the amplitude of the power provided across the cord 112. Although an electrical motor is described, it is to be understood that the motor may be pneumatic, hydraulic, or otherwise powered.

The cam driver 138 is associated with the output shaft 136 and configured to turn with the output shaft 136 at its rotational rate. In the embodiment shown, the cam driver 138 is disposed on the end of the rotation shaft 136, however, in other embodiments, the cam driver 138 is disposed along the length of the output shaft. The cam driver 138 includes a driver surface 144, which in the embodiment shown, faces away from the motor 134. This driver surface 144 has a non-planar surface geometry, described in detail below, that defines the duty cycle of the tissue cutting probe 100.

Figure 3:
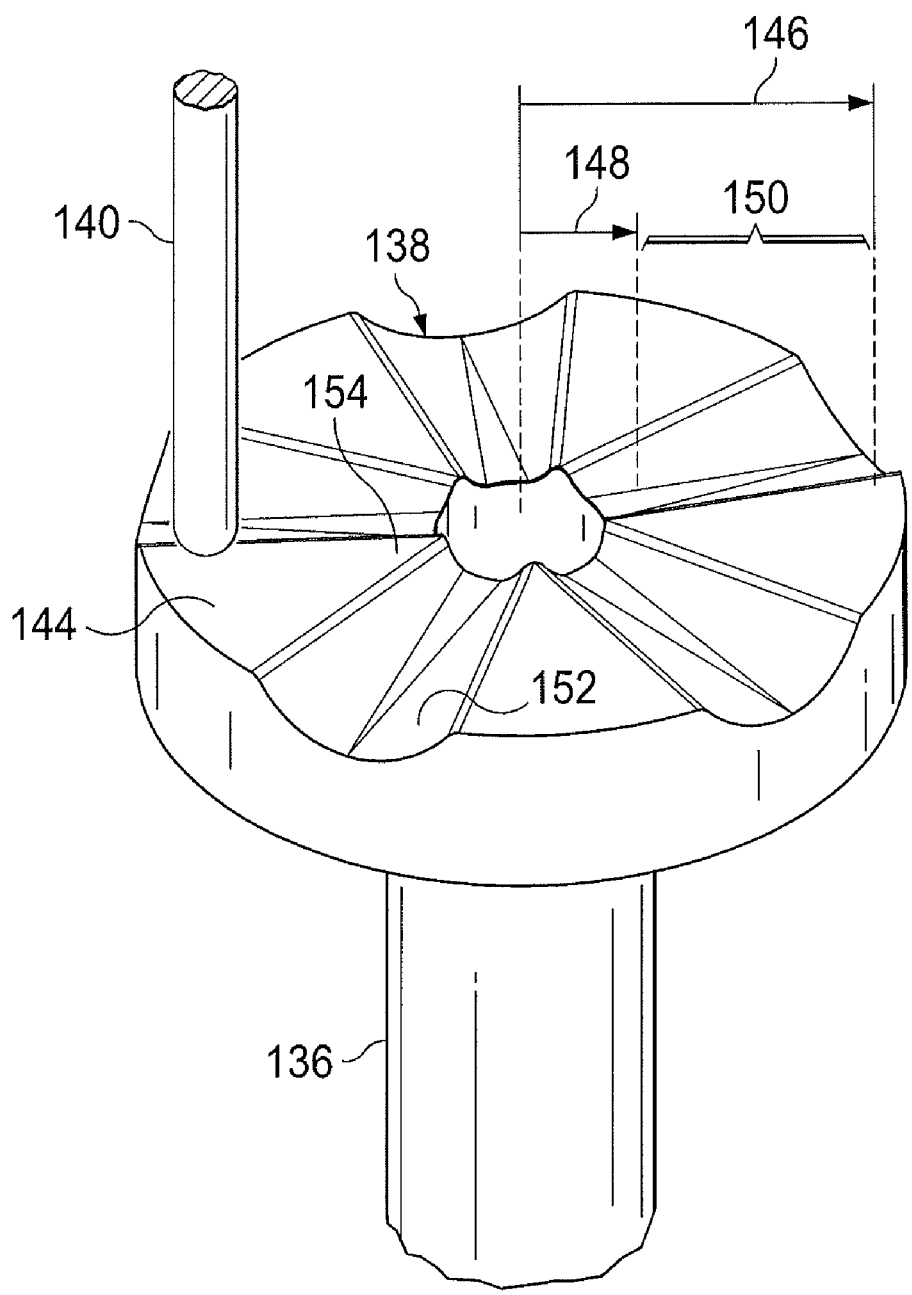
FIG. 3 is an illustration of an exemplary cam driver and follower with the cam driver having surface features that continuously vary between a first geometry at a first radius and a second geometry at a second radius in accordance with the principles and operation herein.

FIG. 3 shows one example of the cam driver 138 with its driver surface 144 having a non-planar surface geometry. In this embodiment, the cam driver 138 appears as a disc disposed on the end of the motor output shaft 136. The disc shape includes the driver surface 144 which, in the embodiment shown, is generally disposed normal or perpendicular to the axis of the output shaft 136.

The driver surface 144 has surface features that vary depending on the radius. In the example in FIG. 3, the surface features dictate the duty cycle, and the variation in surface features enables a health care provider to selectively vary the duty cycle of the probe 100 during use. Because the surface features transition or gradually change as the radius on the cam driver 138 changes, a surgeon can gradually transition or selectively vary the duty cycle as desired. In some examples, the surface features allow the duty cycle to be selectively controlled to vary between an 80% duty cycle (for removing tissue in areas where sensitivities are less pronounced) and a 20% duty cycle (for removing tissue in areas where sensitivities are more pronounced, such as adjacent the retina). Other larger and smaller ranges of control are also contemplated.

Although the surface features continuously vary between a first geometry at a first radius and a second geometry at a second radius, for explanatory purposes only, the driver surface 144 is described relative to an outer radius 146 providing a first duty cycle and an inner radius 148 providing a second duty cycle. The region between these radii is referred to herein as a transition region 150 that includes surface features that continuously vary between the outer radius 146 and the inner radius 148, thereby providing the continuously variable duty cycle. The outer radius 146 has a relatively wavy, non-planar surface geometry with surface features 152. In this example, the surface features 152 have peaks and valleys with the peaks being plateaus extending between the valleys. The inner radius 148 also has a relatively wavy, nonplanar surface geometry with surface features 154. But at the inner radius 148, the surface features 154 have valleys that are wider than the peaks. As will became apparent below, the surface features at each radius selectively interface with the follower 140 and each provides a different duty cycle to the probe 100.

With reference to FIGS. 2 and 3, the follower 140 is configured to interface with and follow the driver surface 144 of the cam driver 138. It is also attached to the inner cutting member 124. Accordingly, rotation of the output shaft 136 spins the cam driver 138, which is followed by the follower 140, which induces an oscillating translational movement in both the follower 140 and the inner cutting member 124. As the inner cutter member 124 moves in an oscillating manner, it may be used to cut tissue as described above.

In the example shown, the follower 140 moves within a bearing sleeve 158 captured within the main housing 102. The bearing 158 provides for smooth oscillating action of the follower 140 as it follows the geometry of the driver surface 144. In this example, a spring 160 biases the follower 140 against the driver surface 144. Accordingly, the follower 140 is responsive to the surface features on the driver surface 144 as the cam driver 138 rotates.

The stroke and the duty cycle of the inner cutting member 124 are related to the surface geometry and profile of the cam driver 138. Conventional systems allow the stroke or duty cycle to be changed only by disassembling the cutter probe and removing and replacing components with alternative components having different angles or profiles. However, the probe 100 disclosed herein permits a user to change the stroke or duty cycle merely by actuating a built in actuating system that changes the contact location of the follower 140 on the cam driver's driver surface 144. For example, when the follower 140 is disposed at the outer radius 146 of the cam driver 138 having the first surface features 152, the follower 140 is driven to correspond with the surface geometry, providing a first duty cycle. In this case, when the follower 140 is disposed at the outer radius 146, the first surface features 152 with the wider peaks and narrower valleys result in the follower being disposed at the peaks for a longer period of time than in the valleys. This results in a lower duty cycle because the port 120 in FIG. 2 is closed for a longer period of time than it is open for each cutting cycle. In one example, the outer radius provides a biased closed duty cycle of 20%. Any duty cycle under 50% is considered biased closed because the port is closed longer than it is open for each cutting cycle.

However, when the follower 140 is disposed at the inner radius 148 of the cam driver 138, the follower 140 is driven to correspond with the second surface features 154 providing a second duty cycle. In this case, when the follower 140 is disposed at the inner radius 148, the second surface features 154 with the wider valleys and narrower peaks result in the follower being disposed at the valleys for a longer period of time than at the peaks. This results in a higher duty cycle because the port 120 in FIG. 2 is open for a longer period of time than it is closed for each cutting cycle. In one example, the inner radius provides a biased open duty cycle of 80%. Because the duty cycle is more than 50%, it is considered biased open.

The transition region 150 between the outer and inner radii 146, 148 continuously transitions from the first surface features 152 providing a 20% duty cycle to the second surface features 154 providing an 80% duty cycle. Accordingly, the follower 140 smoothly transfers between the outer and inner radii 146, 148 to vary the duty cycle between the outer and inner radii 146, 148. In the example shown, the middle radius between the outer and inner radii 154, 156 is configured provide a 50% duty cycle. In some examples, the surface features form a sinusoidal wave, resulting in the 50% duty cycle. Because the change in surface features is continuous across the radius, each radius results in a different duty cycle.

The actuating system 142 is the mechanism that displaces the follower 140 relative to a first radius to a second radius, resulting in a shaft or transfer form a first duty cycle to a second duty cycle. In this embodiment, the actuating system transfers the follower 140 between the outer and inner radius 146, 148. In accordance with this, the actuating system 142 on the probe 100 includes an input 164 and a shifting mechanism 166. In this embodiment, the input 164 is a finger-operated lever on the handpiece 104, and the shifting mechanism 166 is a rigid rod responsive to the lever. The shifting mechanism 166 is configured to interface with the follower 140 to displace or move the follower 140 relative to the driver surface 144. Particularly, the shifting mechanism 166 is configured to selectively and variably move the follower 140 between the surface features 152 on the outer radius 146 and the surface features 154 on the inner radius 148. Doing this enables a user to continuously and variably shift between a first duty cycle or stroke length (defined by the surface features at any first radius) and a second duty cycle or stroke length (defined by the geometry at any second radius). In this instance, the connection between the input 164 and the shifting mechanism 166 may be cam or gear driven in a way to displace the follower 140.

Although disclosed with a moveable lever as the input 164, the actuating system 142 may include any components that allow a user to input and mechanically shift the follower 140 relative to the cam surface. For example, the input device may be a push button, a rotation knob, among other input devices. In addition, in some embodiments, the input is an electrical input that sends a signal to an actuator or electrically driven apparatus that operates to displace the follower 140 relative to the cam surface. Likewise, the shifting mechanism may be any of variety of systems that displace the follower 140. For example, these may include a hydraulic actuator, a motor driven displacement, a manual displacement, a microelectromechanical actuator, a shape memory alloy actuator such as nitonol, a piezo, a solenoid, or a pneumatic actuator, among others. This may also include rods or pushers that mechanically apply loading to the follower 140 to displace it relative to the cam driver 138. In some embodiments the actuator operates on the cam driver 138 instead of the follower 140 to displace the follower and cam surface relative to each other.

In some embodiments, the actuating system 142 that shifts or transfers the follower 140 relative to a first radius to a second radius is a squeezable handle on the probe 100. As a user squeezes the handle, the motor 134 and the cam driver 138 displace relative to the follower 140 to effect a change in the interfacing radius. In such a system, a health care provider may squeeze the handle to increase or decrease the resulting duty cycle while performing a surgical procedure. In some embodiments, the squeezing may drive an actuator that displaces the interface location on the cam driver 138. In some embodiments, the handle may be associated with a position encoder or alternative Hall effect sensor that responds to squeezing of the handle and regulates signals to drive a motor driven shifting mechanism. Other systems are contemplated.

Although described as being continuously variable between a 20% and 80% duty cycle, other embodiments provide a different range of continuously variable duty cycle. For example, some embodiments have surface features that provide a continuously variable duty cycle between 30% and 70%, while others provide a variable duty cycle between 40% and 60%. Others provide a non-symmetric duty cycle range, such as for example, a variable duty cycle range from 20% to 60%. These ranges are exemplary ranges only, and others are contemplated. In each of these examples, the surface features are configured to vary between bias closed and biased open duty cycles. Other embodiments have surface features that maintain the variably duty cycle entirely within the biased closed range, while yet others have surface features that maintain the variably duty cycle entirely within the biased open range.

Figure 4:
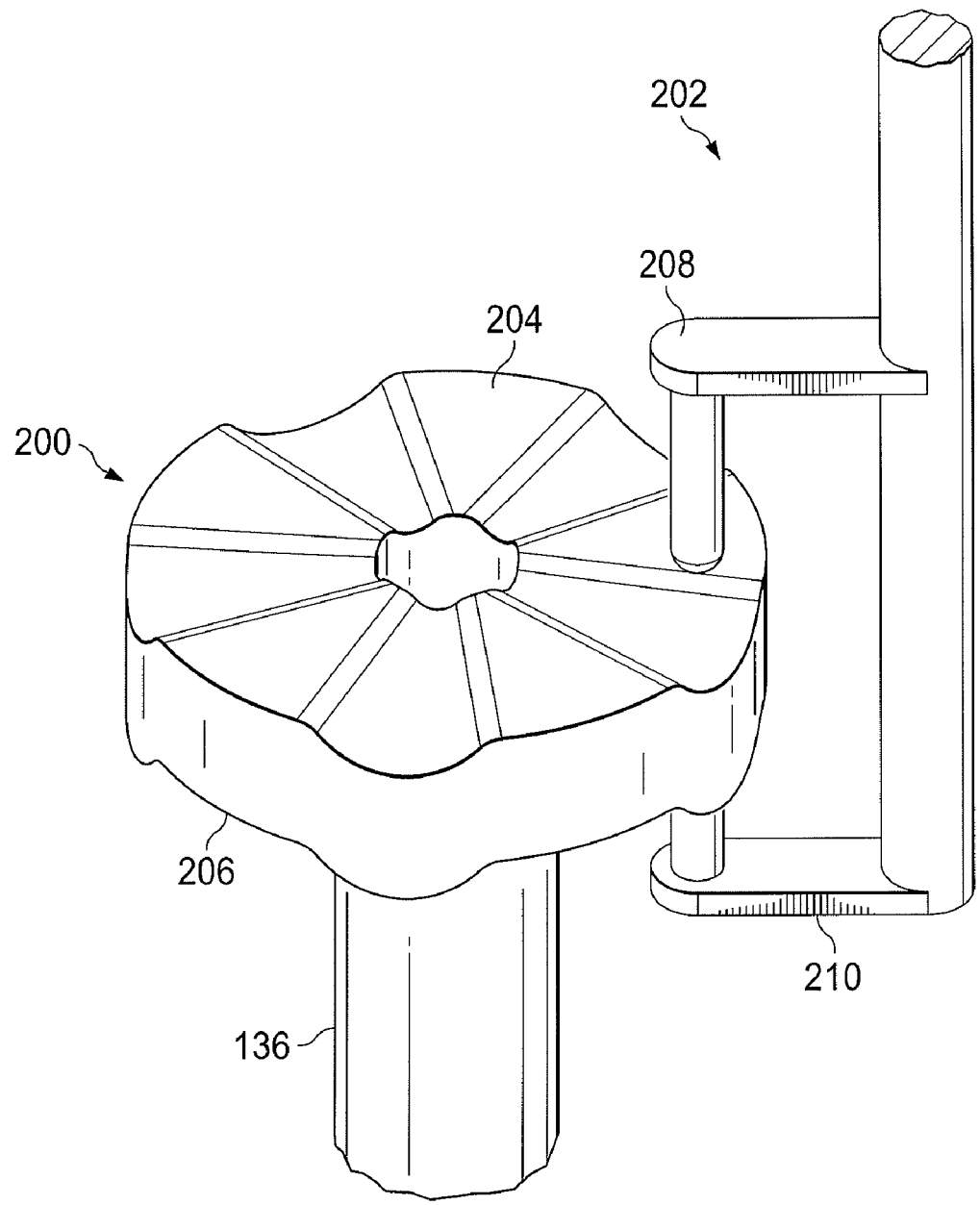
FIG. 4 is an illustration of another exemplary cam driver and follower with the cam driver having surface features that continuously vary between a first geometry at a first radius and a second geometry at a second radius on both sides, and the follower being configured to simultaneously contact both sides of the cam driver in accordance with the principles and operation herein.

FIG. 4 shows an alternative cam driver and follower, referenced herein by the reference numerals 200 and 202, respectively. In this embodiment, the cam driver 200 includes a first cam surface 204 with a surface geometry as explained above that has different features at different radii. In addition, the cam driver 200 includes a second cam surface 206 that has corresponding surface features forming a corresponding geometry at the different radii. Here, the first and second corresponding cam surfaces 204, 206 are on opposing sides of the disc body of the cam driver 200.

The cam follower 202 in this embodiment is arranged to interface simultaneously with both the first and second opposing cam surfaces 204, 206. Accordingly, in this example the cam follower 202 is bifurcated to have a first arm 208 and a second arm 210 that each interface with the opposing surfaces. In this embodiment, both the first and second arms are mechanically configured to continuously contact the cam surfaces 204, 206. Displacing the interface location of the arms 208, 210 from a first radius having a first surface geometry on the cam driver 200 to the second radius having the second geometry changes the duty cycle in the manner described above. This type of arrangement may find particular utility when the motor shaft speed is so high that the spring return mechanism in FIG. 1 becomes unsuitable for maintaining the follower in continuous contact with the driver surface.

Although shown and described as shifting between the outer radius and the inner radius, the shifting may occur between any first and second radii on the driver surface 144. Because the surface features on the driver surface vary at every radius, a user may choose to operate the probe with any duty cycle anywhere between the inner and outer radii as desired. For example, instead of shifting the duty cycle from 80% to 20% duty cycle, the health care provider may shift only part of the way across the driver surface, depending on the desired duty cycle.

In addition to controlling the duty cycle, the surface features directly affect the stroke length. For example, different surface feature depths at different radii result in different stroke lengths at the cutting tube 110, in FIG. 2. Accordingly, the stroke length for the inner cutting member 124 corresponds to the displacement of the depth of the surface geometry. Some embodiments permit a user to change stroke lengths by having surface features with different depths at different radii. Accordingly, a user may shift from one stroke length to another, such as, by way of example, to a stroke length that only partially opens outer port 120. In some embodiments, the duty cycle is maintained at different radii, but the stroke length changes.

In operation, a health care provider activates the motor 134 to operate at a desired motor speed. As explained above, the inner bore 126 of the inner cutting member 124 is fluidly coupled to the aspiration line 114. Inner bore 112 and fluid line 209 are primed with a surgical fluid.

The health care provider inserts the cutting tube 110 into the posterior segment of the eye using a pars plana insertion and selects a desired vacuum level for a vacuum source. Ophthalmic tissue is aspirated into the inner channel 122 of the outer sleeve via the outer port 120. The health care provider selects a desired cut rate for the probe 100 using, for example, a proportional control device (not shown), such as a foot controller. More specifically, the motor 134 is powered to operate at a desired rate to turn the cam driver 138 at a desired speed. The follower 140 responds to the features forming the surface geometry on the cam driver 138 and the inner cutting member 124 moves in a reciprocating manner at the desired cut rate. When the follower 140 is at a low point on the driver surface 144 of the cam driver 138, the outer port 120 is open, and when the follower 140 is at a high point on the driver surface 144 of the cam driver 138, the outer port 120 is closed.

When the health care provider decides to vary the duty cycle, he or she controls the actuator system 142 to move the follower 140 relative to the surface features on the driver face, such as from a first radius with first surface features on the driver surface 144 of the cam driver 138 to a second radius having different surface features. For example, the health care provider may cut and aspirate tissue at a first duty cycle when within the vitreous humor spaced from the retina, and may cut and aspirate tissue at a second duty cycle as the tip approaches the retina. In response to actuating the input 164, the actuating system 142 shifts the follower 140 on the driver surface 144 from the surface features on the cam driver 138 at the first radius to different surface features on the cam driver 138 at a second radius. Because the surface features are different, this results in a change in duty cycle because the amount of time the port is open in a single cutting cycle is directly determined by the surface geometry of the cam driver.

For clarity, it is to be understood, that for a single surface geometry, the duty cycle does not change even when the motor speed changes. Particularly, because the duty cycle is the length of time that the port is open during each cut cycle of probe 100 divided by the total amount of time in each cut cycle, the duty cycle does not change for a faster or slower cut rate. However in the examples shown herein, the changes in duty cycle are accomplished by shifting the follower from a radius having first surface features to a radius having second, different surface features, where the different features result in a change in the length of time that the port is open per the total amount of time in each cut cycle.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A vitrectomy probe having a variable duty cycle cutting mechanism, comprising:
   a motor;
   a cam driver rotationally driven by the motor, the cam driver having a non-planar driver surface having surface features that vary at different radii;
   a follower mechanism arranged to selectively interface with the driver surface at different radii on the driver surface in a manner to selectively interface with the varied surface features at the different radii, the follower being arranged to transfer rotational movement of the cam driver into linear movement of the follower mechanism; and
   a cutting mechanism comprising:
      an outer tubular member having a port configured to receive ophthalmic tissue, and
      an inner tubular cutting member disposed within the outer tubular member, the inner tubular member being associated with the follower mechanism in a manner that the follower mechanism drives the inner tubular cutting member in an oscillating motion;
   wherein the surface features that vary at different radii comprise first surface features at a first radius resulting in a first duty cycle and second surface features at a second radius resulting in a second duty cycle, the first surface features being structurally arranged to provide a biased open duty cycle and the second surface features being structurally arranged to provide a biased closed duty cycle to the cutting mechanism.

2. The probe of claim 1, the non-planar driver surface comprising a continuously variable duty cycle range that includes at least the range of 40 to 60% duty cycle.

3. The probe of claim 1, further comprising an actuating system associated with one of the follower and the cam driver, the actuating system being structurally configured to move the follower and cam driver relative to each other to displace the follower from a position that interfaces with the first surface features at the first radius to a position where the follower interfaces with the second surface features at the second radius.

4. The probe of claim 3, where the actuating system comprises an input mechanism operable by a user and a shifting mechanism that operates in response to the input.

5. The probe of claim 4, wherein the input mechanism is a lever.

6. The probe of claim 1, wherein the non-planar driver surface is configured to displace the inner tubular cutting member relative to the outer tubular member in a manner that only partially opens the port.

7. The probe of claim 1, wherein the non-planar driver surface is a first driver surface, and wherein the cam driver includes a second non-planar driver surface opposing the first driver surface.

8. The probe of claim 7, wherein the follower is structurally configured to simultaneously contact the first and second driver surfaces.

9. The probe of claim 1, wherein the cam driver includes a radius with surface features that are sinusoidal.

10. The probe of claim 9, wherein the radius with surface features that are sinusoidal is disposed midway between the first radius and the second radius.

11. An electric vitrectomy probe having a variable duty cycle cutting mechanism, comprising:
    an electrically powered motor;
    a cam driver rotationally driven by the motor, the cam driver having a non-planar driver surface, the non-planar driver surface having a first radius with surface features resulting in a first duty cycle and a second radius with surface features resulting in a second duty cycle;
    a follower mechanism arranged to interface selectively with both the first radius and the second radius, the follower being arranged to transfer rotational movement of the cam driver into linear movement of the follower mechanism;
    an actuating system associated with one of the follower and the cam driver, the actuating system being structurally configured to move the follower and cam driver relative to each other from a position where the follower interfaces with the first radius of the cam driver to a position where the follower interfaces with the second radius; and
    a cutting mechanism associated with the follower and configured to cut tissue during a vitrectomy procedure.

12. The probe of claim 11, wherein the first surface features are structurally arranged to provide a biased open duty cycle and the second surface features are structurally arranged to provide a biased closed duty cycle to the cutting mechanism.

13. The probe of claim 12, the non-planar driver surface comprising a continuously variable transition region disposed between the first radius and the second radius.

14. The probe of claim 11, wherein the non-planar driver surface is configured to displace the inner tubular cutting member relative to the outer tubular member in a manner that only partially opens the port.

15. The probe of claim 11, wherein the cutting mechanism comprises:
    an outer tubular member having a port configured to receive ophthalmic tissue; and
    an inner tubular cutting member disposed within the outer tubular member, the inner tubular member being associated with the follower mechanism in a manner that the follower mechanism drives the inner tubular cutting member in an oscillating motion.

16. A method of operating a vitrectomy probe having a variable duty cycle cutting mechanism, comprising:
    inserting a cutting tube of the vitrectomy probe into a posterior segment of the eye;
    controlling a motor to rotationally drive a cam driver associated with the motor, the cam driver having a non-planar driver surface, the non-planar driver surface having continuously variable surface features between a first radius with surface features resulting in a first duty cycle and a second radius with surface features resulting in a second duty cycle;
    actuating a system associated with one of a follower and the cam driver, the actuating system being structurally configured to move the follower and cam driver relative to each other from a position where the follower interfaces with the first radius of the cam driver to a position where the follower interfaces with the second radius to change the duty cycle from the first duty cycle to the second duty cycle; and opening and closing a port on a cutting tube in accordance with the first duty cycle when the follower is in contact with the first radius and opening and closing the port in accordance with the second duty cycle when the follower is in contact with the second radius.

17. The method of claim 16, wherein actuating a system comprises:

receiving an input from a health care provider, and shifting the follower relative to the cam driver across a continuously variable transition region between the first radius and the second radius on the cam driver.

18. The method of claim 17, wherein opening and closing a port comprises:

moving a first inner member relative to a port formed in an outer member, the first inner member forming a first cutting mechanism, the first inner member being associated with the follower.

* * * * *